(12) United States Patent
Rausing et al.

(10) Patent No.: US 10,539,088 B2
(45) Date of Patent: Jan. 21, 2020

(54) METHOD AND DEVICE FOR DIAGNOSING AND FOR CALIBRATING AN EXHAUST GAS SENSOR

(71) Applicant: AUDI AG, Ingolstadt (DE)

(72) Inventors: Johannes Rausing, Ingolstadt (DE); Johannes Neukam, Pegnitz (DE)

(73) Assignee: AUDI AG, Ingolstadt (DE)

( * ) Notice: Subject to any disclaimer, the term of this patent is extended or adjusted under 35 U.S.C. 154(b) by 190 days.

(21) Appl. No.: 15/711,520

(22) Filed: Sep. 21, 2017

(65) Prior Publication Data

US 2018/0100462 A1 Apr. 12, 2018

(30) Foreign Application Priority Data

Oct. 6, 2016 (DE) .................. 10 2016 219 387

(51) Int. Cl.
| | |
|---|---|
| *F02D 41/22* | (2006.01) |
| *F01N 11/00* | (2006.01) |
| *F02D 41/14* | (2006.01) |
| *F02D 41/24* | (2006.01) |
| *F01N 13/00* | (2010.01) |

(Continued)

(52) U.S. Cl.
CPC ............ *F02D 41/222* (2013.01); *F01N 11/00* (2013.01); *F01N 13/008* (2013.01); *F01N 13/017* (2014.06); *F01N 13/08* (2013.01); *F02D 41/1439* (2013.01); *F02D 41/1441* (2013.01); *F02D 41/1495* (2013.01); *F02D 41/2474* (2013.01); *G01N 33/0006* (2013.01); *F01N 3/035* (2013.01); *F01N 3/10* (2013.01); *F01N 2560/02* (2013.01); *F01N 2900/1402* (2013.01); *G01M 15/104* (2013.01); *Y02A 50/2322* (2018.01); *Y02T 10/47* (2013.01)

(58) Field of Classification Search
CPC ................. Y02T 10/47; F01N 2560/02; F01N 2900/1402; F01N 13/017; F01N 13/08; F01N 13/008; F01N 3/035; F01N 3/10; F01N 11/00; F02D 41/1441; F02D 41/1495; F02D 41/2474; F02D 41/1439; F02D 41/222; G01M 15/104; G01N 33/0006; Y02A 50/2322

See application file for complete search history.

(56) References Cited

U.S. PATENT DOCUMENTS

| 9,650,981 | B1 | 5/2017 | Large et al. |
| 2013/0276428 | A1 | 10/2013 | Levijoki et al. |
| 2017/0241321 | A1 | 8/2017 | Yoo et al. |

FOREIGN PATENT DOCUMENTS

| CN | 103375235 B | 3/2016 |
| DE | 19842425 C2 | 10/2003 |

(Continued)

OTHER PUBLICATIONS

Examination Report dated May 18, 2017 of corresponding German application No. 102016219387.2; 12 pgs.

(Continued)

*Primary Examiner* — Anthony R Jimenez
(74) *Attorney, Agent, or Firm* — Maier & Maier, PLLC

(57) ABSTRACT

A method for diagnosing and calibrating an exhaust gas sensor. An exhaust gas mass flow generated by an internal combustion engine is divided and a first part of the exhaust gas flow is conducted through a first exhaust gas path of a motor vehicle, and a second part of the exhaust path mass flow is conducted through a second exhaust gas path of the motor vehicle.

8 Claims, 3 Drawing Sheets

(51) Int. Cl.
  *F01N 13/08*   (2010.01)
  *G01N 33/00*   (2006.01)
  *F01N 3/035*   (2006.01)
  *F01N 3/10*    (2006.01)
  *G01M 15/10*   (2006.01)

(56) References Cited

FOREIGN PATENT DOCUMENTS

| | | |
|---|---|---|
| DE | 102006010497 A1 | 9/2006 |
| DE | 102014114976 A1 | 4/2015 |
| EP | 0525566 A1 | 2/1993 |
| EP | 2653683 A1 | 10/2013 |
| EP | 2960453 A1 | 12/2015 |
| JP | H03246456 A | 11/1991 |

OTHER PUBLICATIONS

Office Action dated Jun. 24, 2019, in corresponding Chinese Application No. 201710924138.4 including partial machine-generated English language translation; 9 pages.
Supplementary Search Report dated Apr. 28, 2014, in corresponding European Application No. 10860784.7 (published as EP2653684A4, Jun. 11, 2014); Cited in NPL Cite No. 1; 2 pages.

METHOD AND DEVICE FOR DIAGNOSING AND FOR CALIBRATING AN EXHAUST GAS SENSOR

FIELD

The present invention relates to a method for diagnosing and calibrating an exhaust gas sensor, an exhaust gas system and a computer program.

BACKGROUND

During the after-treatment of exhaust gases of an internal combustion engine, the exhaust gas sensors that are arranged according to respective exhaust gas elements, such as filters and catalytic converters for after-treatment, are very important for a pollutant-optimized operation of the internal combustion engine.

Exhaust gas sensors are generally employed to monitor exhaust gas values before and after respective exhaust gas after-treatment elements and to ensure that legal requirements, which are defined for example by limiting value for exhaust gas values, are complied with. Accordingly, exhaust gas sensors are often prescribed by legal statutes for controlling the operation of an internal combustion engine.

In order to make it possible to ensure a correct functioning of respective exhaust gas sensors, the sensors are calibrated during the operation of an internal combustion engine based on specifically defined exhaust gas concentrations. For this purpose, the function of the exhaust gas sensor must be according to legal statutes verifiable during the operation of the internal combustion engine.

In order to test the function of an exhaust gas sensor, an exhaust gas system is impacted with a defined exhaust gas amount and concentration of pollutants. The exhaust gas values obtained during the impacting of the exhaust gas sensor, such as for example concentrations of pollutants, are then compared to a predetermined target value in order to infer therefrom malfunctions and/or deviations in the measurement behavior of the exhaust gas sensor. So as to examine the exhaust gas sensors and the elements of the after-treatment of the gas sensors arranged in a exhaust gas system, it is necessary to temporarily suppress the elements for post treatment of the exhaust gas and to impact the exhaust gas sensors with untreated exhaust gas.

As statutory requirements become more and more strict, it can sometime occur that the concentration in a stream of exhaust gas which is used with exhaust gas sensors arranged behind the respective elements for post treatment of exhaust gas exceeds the legally prescribed limiting value for a concentration of pollutants, so that a corresponding exhaust gas system generates during the examination of respective exhaust gas sensors of the exhaust gas system a value that exceeds the legally prescribed limiting value. Accordingly, there is a need for a method for diagnosing an exhaust gas sensor arranged behind respective exhaust gas post treatment elements of an exhaust gas system while remaining in compliance with applicable regulations for exhaust gas.

The European patent document EP 2 960 453 A1 discloses an exhaust gas system that is provided with a main line and with a secondary line.

In the European patent document EP 0 525 566 A1 is described an exhaust gas system that is provided with a plurality of filters.

The German patent document DE 2006 010 497 A1 discloses a exhaust gas system provided with an exhaust gas path, which is equipped with a first filter and with a second filter arranged in the direction of the flow downstream of the first filter.

SUMMARY OF THE DISCLOSURE

Against this background, the objective of the present invention is to make it possible to diagnose exhaust gas sensors arranged after exhaust gas post treatment elements of an exhaust gas system, while being in compliance with predetermined limiting values for emission of pollutants.

In order to solve the objective mentioned above, a method for diagnosing and calibrating an exhaust gas system is provided, wherein the flow of the exhaust gas mass generated by an internal combustion engine is divided and the first part of the exhaust gas mass flow is conducted through a first exhaust gas path of a motor vehicle, and a second part of the exhaust gas flow is conducted through a second exhaust gas path, and wherein the first exhaust gas path and the second exhaust gas path each comprise at least one exhaust gas post treatment element and at least one exhaust gas sensor arranged in the flow direction of the exhaust gas mass flow after at least one exhaust gas post treatment element, and wherein an exhaust gas post treatment output of the at least one exhaust gas post treatment element of the first exhaust gas is smaller than an output of the exhaust gas post treatment element of the second exhaust gas path, and wherein by comparing at least one of the first exhaust gas path pollutant values determined by the exhaust gas sensor to the exhaust gas path pollutant value determined by the pollutant value determined for the other exhaust gas path, the detected pollutant values are compared and based on this comparison, a diagnosis is established for the first exhaust gas path and for the second exhaust gas path and at least one exhaust gas sensor of the second exhaust gas path is calibrated.

An embodiment will become apparent from the description and from the dependent claims.

In the context of the present invention, the term "pollutant" value describes a value of a proportionate amount of pollutants in an exhaust gas flow, which is to say a concentration of pollutants.

In the context of the present invention, the term exhaust gas post treatment output is to be understood as an ability to reduce emissions in a predetermined exhaust gas flow.

The method described is used in particular to diagnose and/or to calibrate exhaust gas sensors of an exhaust gas system. According to the invention, one of the exhaust gas currents generated by an internal combustion machine is divided and conducted into a first part of the exhaust gas mass flow through a first exhaust gas path, and a second part of the exhaust gas mass currents is conducted through a second exhaust gas path. In this case, it is further provided that the respective exhaust gas post treatment elements arranged in the second exhaust gas path have a reduced exhaust gas post treatment output compared to the exhaust gas post treatment element arranged in the first exhaust gas path, so that the exhaust gas post treatment elements arranged in the first path can be passed through it faster and easier, which is to say it can expel untreated exhaust gas faster than the exhaust gas post treatment element arranged in the second exhaust gas path. For this purpose, the exhaust gas post treatment elements arranged in the first exhaust gas path can for example have a smaller surface area or a smaller volume than the exhaust gas post treatment elements that are arranged in the second exhaust gas path.

Under an exhaust gas post treatment element is in the context of the present element invention to be understood an element in an exhaust gas path by means of which the exhaust gas generated by the internal combustion engine is post-treated so that as a result, the pollutants in the exhaust gas are reduced. An exhaust gas post treatment element comprises for example a filter and/or a catalytic converter. Accordingly, under an exhaust gas post treatment output is to be understood the reduction of pollutants or emissions achieved in an exhaust gas pertaining to a certain period of time.

Under an exhaust gas sensor is in the context of the present invention to be understood a sensor, such as for example a lambda sensor, which is designed to detect exhaust gas values, i.e. the values of pollutants in an exhaust gas. The exhaust gas sensor arranged in the second exhaust gas path according to the invention and the exhaust gas sensor arranged in the first exhaust gas path according to the invention are the same type of sensor, which is to say that both of these exhaust gas sensors are for example linear broadband sensors.

Under a limiting value for a concentration of pollutants is in the context of the present invention to be understood a maximum permissible quantity of pollutants in a specific exhaust gas flow.

In order to calibrate or test the exhaust gas generated by an internal combustion engine with exhaust gas sensors arranged behind respective exhaust gas post treatment elements based on the untreated exhaust gas flow, i.e. based on the maximum permissible quantity of pollutants contained in an exhaust gas flow, the internal combustion engine is switched to an operating state in which the internal combustion engine generates exactly so much exhaust gas that exhaust gas post treatment elements arranged in the first exhaust gas path are overwhelmed, which is to say that exhaust gas post treatment element arranged in the first exhaust gas path are overloaded or loaded up to the maximum. Accordingly, the exhaust gas sensors arranged behind the exhaust gas post treatment element which are arranged in the first exhaust gas path are impacted with the untreated exhaust gas, or with the maximum quantity of the polluted exhaust gas. Based on the untreated exhaust gas, which in particular displays a concentration of pollutants that is above a legally permissible limiting value, the exhaust gas sensors arranged in the first exhaust gas path behind the exhaust gas post treatment elements can be calibrated or tested.

In order to calibrate exhaust gas sensors arranged behind the corresponding exhaust gas post treatment element in a respective first exhaust gas path, the respective measured values of the exhaust gas sensor, which are detected when the sensors are impacted with untreated gas, are assigned a maximum value of for example "1", so that the measured values can then be standardized based on the value of "1".

In order to test an exhaust gas sensor arranged in a respective first path behind a corresponding exhaust gas post treatment element, the respective measured values of the exhaust gas sensor can be adjusted based on specified limiting values. If the value determined is below or above the limiting value, an error signal can be generated.

In order to diagnose an exhaust gas sensor arranged in a respective exhaust gas path behind a corresponding exhaust gas post treatment element, a currently determined proportionality factor can be matched to a diagnosed value so that when a specified threshold value is exceeded by the amount of the difference determined during the matching, an error is generated. The amount of the difference is in this case the difference between the currently determined proportionality factor and the diagnosed value.

According to the invention it is provided that the performance of an exhaust gas post treatment carried out by the exhaust gas post treatment elements provided in the second exhaust gas path according to the invention is proportional to the performance of the exhaust gas post treatment carried out with the exhaust gas post treatment elements provided according to this invention in the first exhaust gas path. If is further provided that the exhaust gas post treatment performed in the second exhaust gas path is independent of the exhaust gas post treatment performed in the first exhaust gas path.

By using the method described above, the exhaust gas post treatment systems used for post treatment of exhaust gases that are connected downstream of the respective exhaust gas sensors for calibration or testing of the generated exhaust gases are no longer necessary.

In a possible embodiment of the described method it is provided that the flow of the exhaust gas passing through the first exhaust gas path is divided in such a way that a volume of the exhaust gas flow conducted through the first exhaust path is smaller than a volume of the exhaust gas flow that is conducted through the second exhaust path.

In order to select the load of the pollutants created by an exhaust gas for testing or calibrating purposes in such way that the exhaust gas will overwhelm the exhaust gas post treatment elements, while still keeping it as small as possible, it is in particular provided that the first exhaust gas path is designed to be significantly smaller than the second exhaust gas path. By means of a first exhaust gas path, which is reduced in size with respect to the second exhaust gas path, the flow of the exhaust gas mass conducted through the first exhaust gas path is also reduced compared to the flow that is conducted through the second exhaust gas path, which is according to the invention fully post-treated by the exhaust gas post treatment elements in the second exhaust gas path.

In another possible embodiment of the described method it is provided that the internal combustion engine is switched to an operating mode in which the exhaust gas system is impacted with an exhaust gas having a concentration of pollutants resulting in that at least one exhaust gas sensor of the first exhaust gas path is exposed to a quantity of pollutants that is higher than a predetermined limiting value. In this case, it is provided that during the operation of the internal combustion engine in the operating mode, a total pollutant emission will remain below a specified limiting value. For this purpose, the exhaust gas of the second exhaust gas path is calibrated based on the exhaust pollution measurement values determined during exposure to an impact of the exhaust gas load provided by at least one exhaust gas sensor of the first exhaust gas path according to the invention, wherein the measured value determined with the exhaust gas load of at least one exhaust gas sensor of the second exhaust gas path is corrected and standardized during the impacting of the at least one exhaust gas sensor of the first exhaust gas path by means of the proportionality factor provided according to the invention.

In order to calibrate an exhaust gas sensor arranged in a respective second exhaust gas path behind a corresponding exhaust gas post treatment element, i.e. a second exhaust gas sensor, it is provided that based on a comparison of a measured value of an exhaust gas sensor arranged for calibration in a corresponding first exhaust gas path behind a corresponding exhaust gas post treatment element, which is to say a first exhaust gas sensor that is compared to measured gas values obtained with the second exhaust gas sensor in the second exhaust gas path. Based on this comparison, at least one proportionality factor is calculated. A value can be inferred by means of at least one proportionality factor, which corresponds to a measured value that would be determined by the second exhaust gas sensor when it is impacted by untreated exhaust gas. Accordingly, the second exhaust gas sensor can be calibrated by means of the proportionality factor on the basis of the values determined by the first exhaust gas sensor.

In another possible embodiment according to the invention of the method described, it is provided that the internal combustion engine is switched to an operating mode in which the exhaust gas system is impacted with the exhaust gas that has a concentration of pollutants that results in at least one exhaust gas sensor of the first exhaust gas path being impacted by a concentration of pollutants that is higher than a specified limiting value. In this case it is provided that a concentration of the pollutants of a total exhaust gas system expelled from exhaust gas system, i.e. the concentration of pollutants in exhaust gas system that is composed of the exhaust gas mass flow expelled from the first exhaust gas path and from an exhaust gas mass flow expelled from the second exhaust gas path remain under the predetermined limiting value.

It is further also provided that at least one exhaust gas sensor of the second exhaust gas path is tested based on the respective measured value determined with the exhaust gas during the impacting of at least one exhaust gas sensor of the second exhaust gas path, wherein the measured value determined with the exhaust gas of the first exhaust gas path during the impacting of the at least one exhaust gas sensor is corrected with at least one proportionality factor and a correspondingly corrected measured value is compared to a respective highest value.

In order to test the second exhaust gas sensor, it is provided that during a test of the first exhaust gas sensor, the measured values determined for the second exhaust gas are corrected or extrapolated by means of at least on proportionality factor and compared to the respective specified highest values. The highest values may be for example the legally prescribed limiting values for the respective values of pollutants to be measured in an exhaust gas mass flow.

As an alternative it is also conceivable that a proportional amount of a total exhaust gas mass stream is matched to or corrected with a specified highest value of a total exhaust gas mass stream. For this purpose, the corrected highest values are calculated by means of the specified highest value and a respective proportionality factor. Accordingly, the corrected highest values are adjusted directly with the exhaust gas values determined by the second exhaust gas sensor.

To determine the at least one proportionality factor, respective measured values detected by a first exhaust gas sensor can be used in a mathematical formula for measured value determined by the second exhaust gas sensor. It goes without saying that a plurality of proportionality values, or a proportional curve, or a proportionality function can be also used determined in order to form for example a non-linear relationship between the measured values determined by the first exhaust gas sensor and the measured values determined by the second gas sensor.

The method described is based essentially on the fact that a small part of an exhaust gas flow is branched off into the first exhaust gas path and a traditional calibration or testing method process is carried out there, and based on a fixed proportionality between the gas post treatment output exhaust gas post treatment elements of the first exhaust gas path to the output of the exhaust gas post treatment of the exhaust gas post treatment of the second exhaust gas path, a calibration or verification of the exhaust gas sensors of the second exhaust gas path is enabled. Accordingly, in order to carry out the described method, the output of the exhaust gas post treatment of the first exhaust gas path must be proportional to the output of the exhaust gas post treatment of the first exhaust gas path. In order to verify the proportionality of the outputs of an exhaust gas post treatment of a respective first and of the second exhaust gas path and to carry out a corresponding diagnosis of each respective exhaust gas system, it is provided that an exhaust gas system is diagnosed as faulty when at least one proportionality factor deviates from at least one specified value by an amount that is greater than a specified threshold value.

The present invention further also relates to an exhaust gas system for an internal combustion engine comprising a control device, a first exhaust gas path and a second exhaust gas path, wherein the first exhaust gas path includes at least one exhaust gas post treatment element, the performance of which is reduced compared to the output of an exhaust gas post treatment of an exhaust gas post treatment element of the second exhaust gas path, wherein the first exhaust gas path and the second exhaust gas path comprise at least one exhaust gas sensor arranged after a respective exhaust gas post treatment element for the exhaust gas to be generated in the direction of at least one flow of the exhaust gas generated by the internal combustion engine, and wherein the control device is configured to compare the pollutant values detected by at least one exhaust gas sensor of the first exhaust gas path of a first part of an exhaust gas flow generated by an internal combustion engine to the pollutant values of an exhaust gas flow detected by a second exhaust gas sensor in a second exhaust gas path, and to determine at least one proportionality factor between the pollutants detected by at least one exhaust gas sensor of the first exhaust gas path and the pollutants detected in the second exhaust gas path by at least one exhaust gas sensor, and to issue a diagnosis of the exhaust gas system based on the at least one proportionality factor. The described exhaust gas system serves in particular for carrying out the method described above.

In a possible embodiment of the described method, it is provided that the first exhaust gas path and the second exhaust gas path are deployed within an exhaust gas post treatment module. In order to provide an exhaust gas system that is as compact as possible, a gas exhaust post treatment component such as for example a medium jar or a catalytic converter is included as a structural component of the second exhaust gas path provided according to this invention. The exhaust gas module can comprise for example a cylinder that is filled with a filter element, in which a separating wall is arranged in the direction of the flow of the exhaust gas generated by a respective internal combustion engine, which divides the cylinder into a smaller area or a first exhaust gas path, and into a larger area or a second exhaust gas path. By using a simplified element, an element with a smaller reaction surface, or an element with a smaller reactivity, the first exhaust gas path is reduced in its efficiency relative to the second exhaust gas path in such a manner that both exhaust gas paths behave differently but proportionally relative to one another in their exhaust gas post treatment performance.

It goes without saying that the exhaust gas module can be designed in addition to a cylinder or tube shape also with another technically suitable shape.

In another possible embodiment of the described exhaust gas system it is provided that the first exhaust gas path and the second exhaust gas path are designed as structures that are spatially separated from one another. The present invention further relates also to a computer program provided with program code means that are suitable for configuring a computing unit in order to read out measured values determined by the described exhaust gas system and to compare the measured values determined by at least one exhaust gas sensor of the first exhaust gas path to the measured values determined by the at least one exhaust gas sensor of the second exhaust gas path, and to calculate on the basis of this comparison a proportionality factor and generate a fault report when at least one proportionality factor deviates from a specified limiting value by an amount that is greater than a specified threshold value.

The described computer program is used in particular to carry out the described method.

Further advantages and embodiments of the invention will become apparent from the description and from the attached drawing.

It goes without saying that the features mentioned above and those that are still to be explained below can be used not only in their respective combinations shown here, but also in other combinations or in a single setting without deviating from scope of the present invention.

BRIEF DESCRIPTION OF THE DRAWINGS

The invention will be now described in detail based on embodiments schematically illustrated in the figures.

DETAILED DESCRIPTION OF THE DRAWINGS

Figure 1:
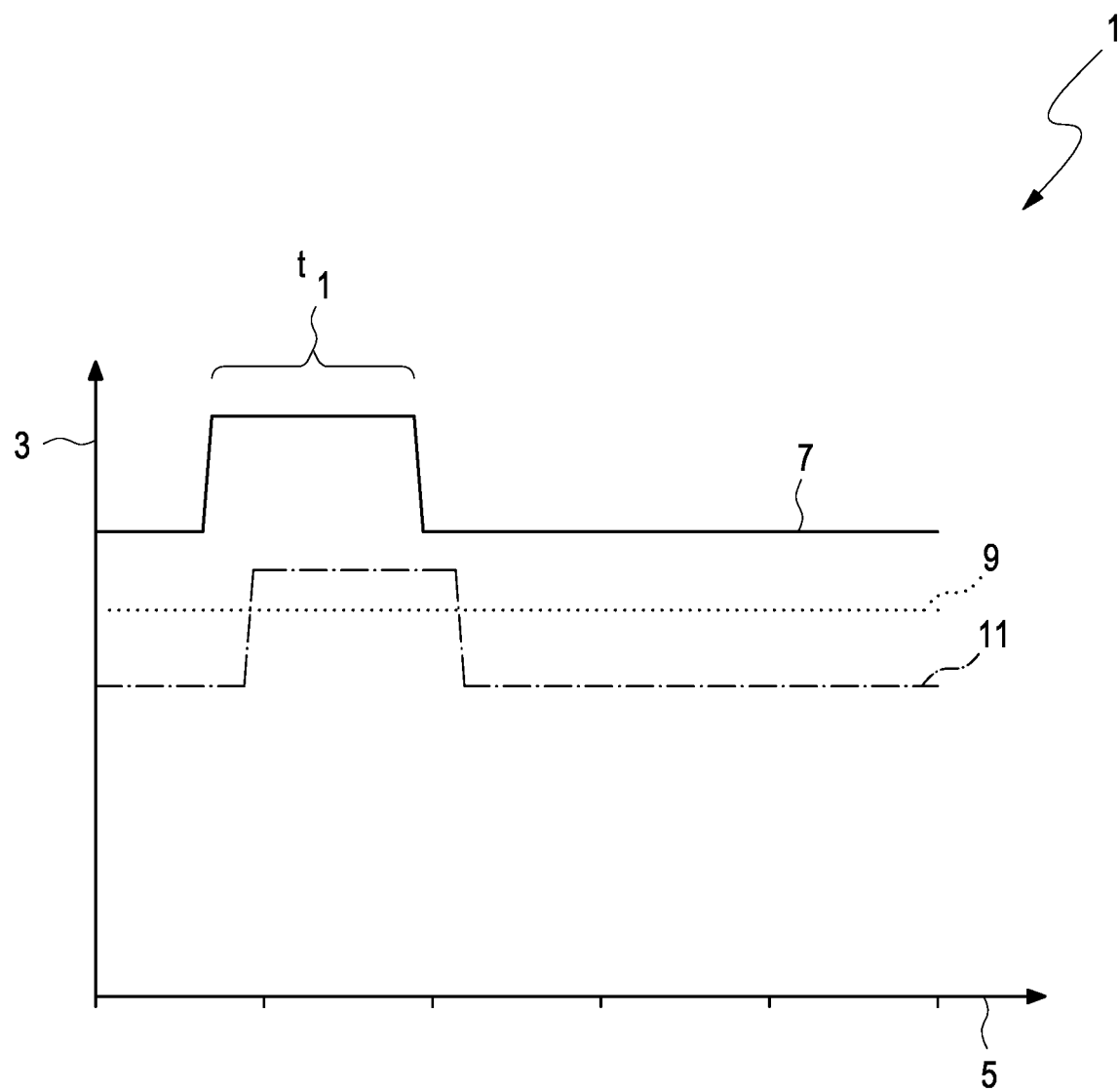
FIG. 1 shows the progress of a concentration of pollutants in an exhaust gas during a calibration process of an exhaust gas sensor according to prior art.

FIG. 1 shows a diagram 1 which shows the concentration of pollutants on the vertical axis 3 while the time elapsed is shown on the horizontal axis 5.

In order to calibrate or verify a gas exhaust system, an exhaust gas mass flow is generated by an internal combustion engine that has during a time window a higher content of pollutants, i.e. a higher concentration of pollutants that is shown by line 7, which indicates a concentration of pollutants in the direction of the flow of the exhaust gas generated by an internal combustion engine of an exhaust gas post treatment element of the exhaust gas system.

As the exhaust gas post treatment element of the exhaust gas system are overloaded by the concentration of pollutants generated during the time window t1, the exhaust gas sensor of the exhaust gas post treatment elements arranged behind the exhaust gas post treatment elements are impacted by the exhaust gas generated in the flow direction by the internal combustion engine as indicated by the line 11. In this case, the concentration of pollutants exceeds during the time window t1 a legally predetermined limiting value, which is shown by the line 9.

Figure 2:
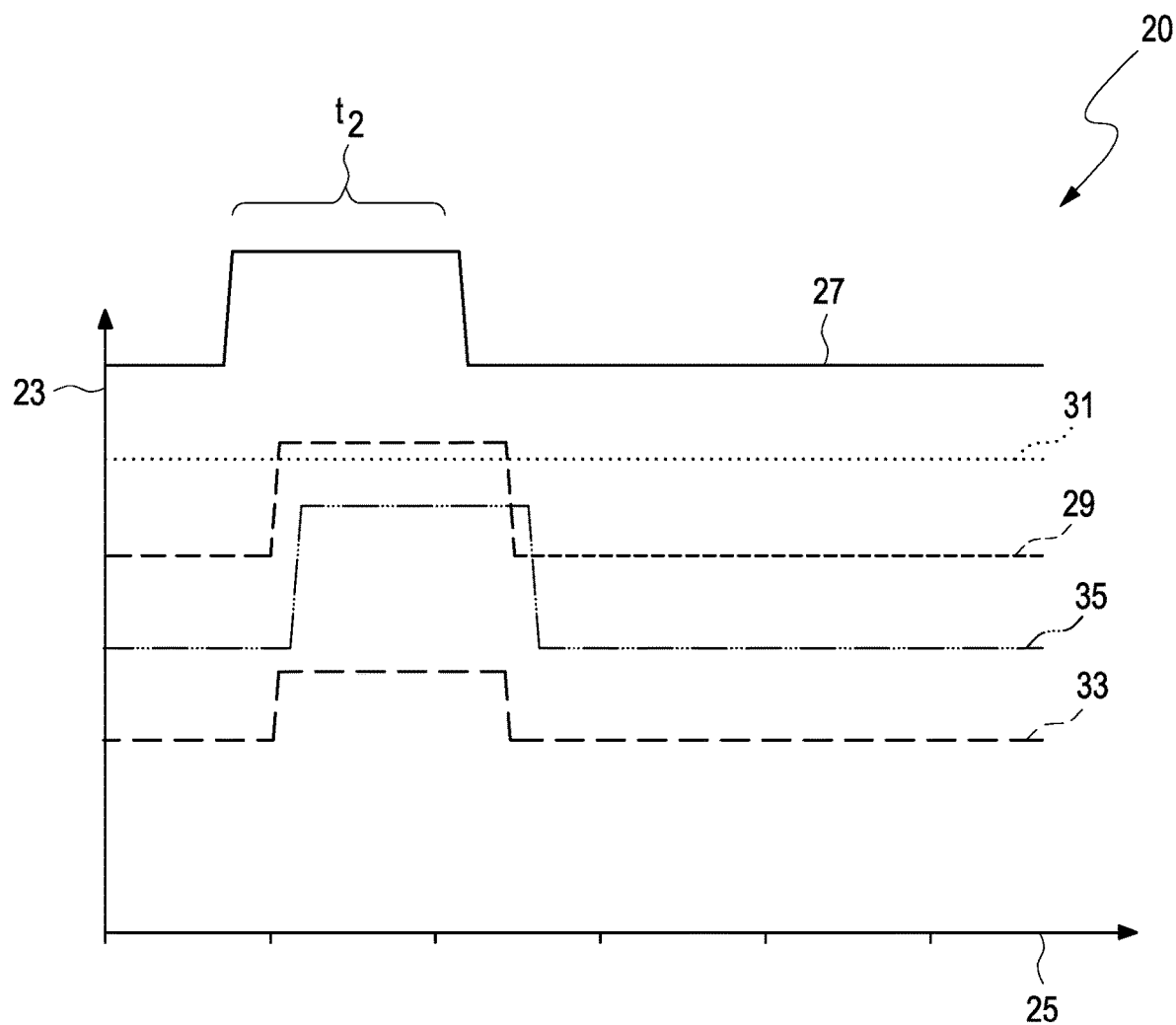
FIG. 2 shows the progress of a concentration of pollutants in an exhaust gas with a calibration process according to one possible embodiment of the method according to the invention.

FIG. 2 shows a diagram 20 in which a concentration of pollutants is shown on the vertical axis 23 over time as indicated on the horizontal axis 25.

In order to calibrate or verify the exhaust gas sensors of an exhaust gas system, an exhaust gas mass flow is generated by an internal combustion engine which has during a time window t2 an increased concentration of pollutants as indicated by the line 27. The line 27 represents a concentration of pollutants in the flow direction of exhaust gas of the internal combustion engine before the respective exhaust gas post treatment element of the exhaust gas system.

Before exhaust gas mass flow generated by the internal combustion engine reaches the respective exhaust gas post treatment elements of the exhaust gas system, the exhaust gas mass flow is divided or split, for example by means of a baffle, into a first exhaust gas flow with a smaller volume or with a smaller volume flow, and into a second exhaust gas mass flow that has a correspondingly larger volume or higher volume flow.

The first exhaust gas flow is conducted into a first exhaust gas path, and the second exhaust gas flow is conducted into a second exhaust gas path. In this case, an exhaust gas post treatment output, which is to say the amount of the exhaust gas that has been post treated with the exhaust gas post treatment elements, is reduced during a specified period of time in the first exhaust gas path in relation to the output of the exhaust gas post treatment of the second output exhaust gas path.

The exhaust gas sensor is in the first exhaust gas path impacted with the exhaust gas earlier as a result of the exhaust gas post treatment capacity of the exhaust gas post treatment element of the first exhaust gas path, which is reduced relative to the exhaust gas post treatment capacity of the exhaust gas post treatment element of the second exhaust gas path, and it has a concentration of pollutants that is above the specified limiting value, which can no longer be post treated by the exhaust gas post treatment element arranged therein, unlike in the case of the second exhaust gas path.

Accordingly, an exhaust gas sensor that is arranged in the flow direction in the first exhaust gas path after the exhaust gas post treatment element is impacted by the untreated exhaust gas or by a concentration of pollutants that is above the legally specified limiting value indicated by the line 29, which is illustrated by line 31. At the same time, an exhaust gas sensor that is arranged in the flow direction of the exhaust gas generated by the respective exhaust gas post treatment element of the second exhaust gas path, is impacted with exhaust gas having a concentration of pollutants that lies below the predetermined limiting value, i.e. with an exhaust gas that was post treated by the exhaust gas post treatment element of the second exhaust gas path, as shown by the line 33.

Since the exhaust gas sensor of the first exhaust gas path has been impacted by an exhaust gas that has not been treated by an exhaust gas post treatment element, the exhaust gas sensor or its maximum value corresponding to the impact of the untreated gas can be standardized or calibrated.

In order to calibrate the second exhaust gas path, the respective measured values determined by the first exhaust gas sensor as shown by the line 33 during the calibration of the exhaust gas sensor of the first exhaust gas path are adjusted based on the measured value of the second exhaust gas path are determined during the calibration of the exhaust gas sensor of the first exhaust gas path as shown by line 29, and a proportional factor is determined based on this adjustment.

Since the exhaust gas post treatment elements of the first exhaust gas path are selected in such a way that they show an exhaust gas post treatment capacity that is proportional in their exhaust gas post treatment capacity to that of the exhaust gas post treatment elements of the second exhaust gas path, the measured values of the exhaust gas sensor of the second exhaust gas path can be inferred based on the proportionality factor obtained by means of values that were measured with the exhaust gas sensor of the first exhaust gas path with a corresponding impact of the pollutants, or with a corresponding load of the exhaust gas containing pollutant.

The exhaust gas sensor of the second exhaust gas path can thus be standardized or calibrated based on the expected measurement value resulting from the impact by untreated exhaust gas. In this case, a concentration of pollutants emitted through the exhaust gas system as indicated by the line 35 is during the entire procedure below the legally prescribed limiting value, which is indicated by the line 31.

Figure 3:
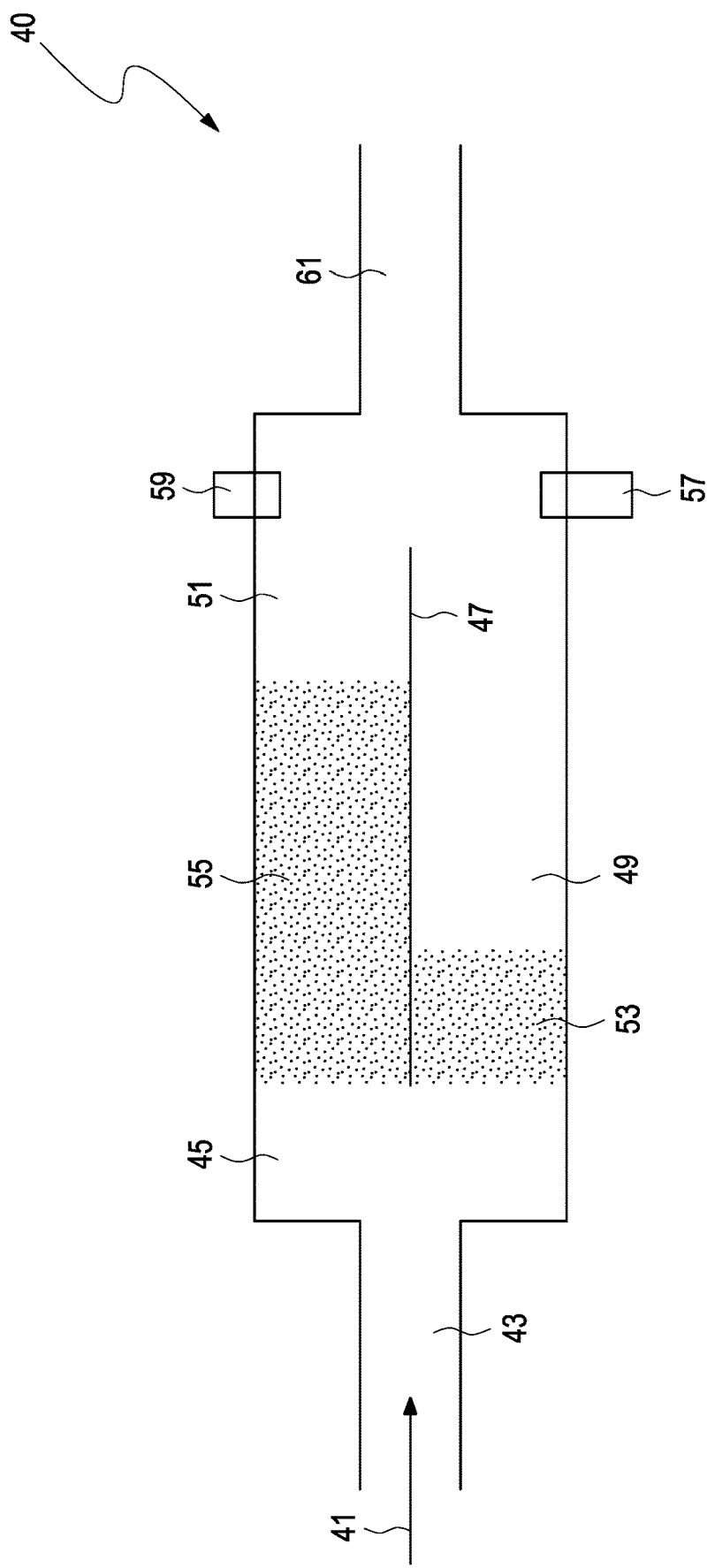
FIG. 3 shows a schematic illustration of a possible embodiment of the gas exhaust system according to this invention.

FIG. 3 illustrates an exhaust gas system 40. An exhaust gas stream generated by an internal combustion engine flows as indicated by the arrow 41 unfiltered into an exhaust gas line 43. On its way through an exhaust gas module 45, the exhaust gas flow is divided by a baffle 47, so that a first part of the exhaust gas flow is conducted along the first exhaust gas path 49, and a second part is conducted along a second exhaust gas path 51 through the exhaust gas module. Since the exhaust gas post treatment with the exhaust gas post treatment output of an exhaust gas post treatment element 53 of the exhaust gas path 49 is smaller than the exhaust gas post treatment output of the exhaust gas post treatment element 55 of the second exhaust gas path 51 as indicated by the shading of the exhaust gas post treatment elements 53 and 55, an exhaust gas sensor 47 which is arranged after the exhaust gas post treatment element 53 of the first exhaust gas path 49 will be impacted with the exhaust gas already at a point in time that has an increased concentration of pollutants at which the exhaust gas sensor 59 arranged after the exhaust gas post treatment element 55 is not yet impacted with the post treated exhaust gas. This means that the exhaust gas sensor 57 in the first exhaust gas path 49, which has a reduced exhaust gas post treatment capacity of the exhaust gas post treatment element 53 relative to the exhaust gas post treatment element 55, will be impacted with exhaust gas at an earlier point, because the exhaust gases are collected faster in the first exhaust gas path 49, which may no longer be post treated by the exhaust gas post treatment element 53 compared to the case of the second exhaust gas path 51.

Since the conduct of the exhaust gas post treatment output of the exhaust gas post treatment element 53 of the first exhaust gas path 49 is proportional to the conduct of the output of the exhaust gas post treatment element 55 of the second exhaust gas path 51, based on the measured values, which were determined by the exhaust gas sensor 59 while the exhaust gas sensor 57 was impacted by the exhaust gas, it is concluded that the values were measured by the exhaust gas sensor 59 when the exhaust gas sensor 59 was impacted when a higher concentration of pollutants was displayed. Should the measurement values determined by the exhaust gas sensor 59 not be proportional, or not have a proportional factor determined in advance to the respective measured values determined by the exhaust gas sensor 57, it can be assumed that the exhaust gas sensor 59 or the exhaust gas post treatment element 55 is defective. In this case, during the entire procedure, including also during the impacting of the exhaust gas sensor 57 with exhaust gas which has a higher concentration of the pollutants, a legally prescribed limiting value for a concentration of the pollutants emitted by the entire exhaust line 61 is not exceeded because the flow of the exhaust gas conducted through the first exhaust gas path 49 has a smaller volume than the flow of the exhaust gas conducted through the second exhaust gas 51.

The invention claimed is:

1. A method for diagnosing and calibrating an exhaust gas sensor, comprising:
 a mass flow of exhaust gas generated by an internal combustion engine is conducted through a first exhaust gas path of a motor vehicle, and a second part of the exhaust gas flow is conducted through a second exhaust gas path of the motor vehicle, wherein the first exhaust gas path and the second exhaust gas path have at least one exhaust gas post treatment element and at least one exhaust gas sensor arranged in a flow direction of the exhaust gas mass flow after the at least one exhaust gas post treatment element, wherein an exhaust gas post treatment output of the at least one exhaust gas post treatment element of the first exhaust gas path is smaller than an output of the exhaust gas post treatment of the at least one exhaust gas post treatment element of the second exhaust gas path and wherein pollutants detected by at least one exhaust gas sensor comprised in the first exhaust gas path are compared to pollutant values detected by the at least one exhaust gas sensor of the second exhaust gas path, and at least one proportionality factor is determined between the pollutant values determined by the at least one exhaust gas sensor of the first exhaust gas path, and the pollutant values detected by the at least one exhaust gas sensor of the second exhaust gas path, and based on a matching of a specified diagnostic value to at least one proportionality factor, a diagnosis of an exhaust gas system is issued, having the first exhaust gas path and the second exhaust gas path, or wherein the at least one exhaust gas sensor of the second exhaust gas path is calibrated,
 wherein the exhaust gas mass flow is divided and a volumetric flow conducted through the first exhaust gas path is smaller than the volumetric flow conducted through the second exhaust gas path.

2. The method according to claim 1, wherein the exhaust gas system is diagnosed as being faulty when the at least one proportionality factor deviates by an amount of at least a specified exceeding value which is greater than a specified threshold value.

3. The method according to claim 1, wherein the internal combustion engine is switched into an operating mode in which the exhaust gas system is impacted with an exhaust gas that has a concentration of pollutants wherein at least one exhaust gas sensor of the first exhaust gas path is exposed to a concentration of pollutants that is higher than a specified limiting value, wherein the concentration of pollutants of a total exhaust gas mass flow emitted by the exhaust gas system remains below the predetermined limiting value, and wherein the at least one exhaust gas sensor of the second exhaust gas path is tested based on a mass value determined with the exhaust gas impact of the first exhaust gas path of the at least one exhaust gas sensor, wherein the at least one exhaust gas sensor of the second exhaust gas path is tested by respective measured values determined by the at least one exhaust gas sensor of the first exhaust path while being impacted by the exhaust gas, and wherein the measured values are corrected by the at least one proportionality factor and the correspondingly corrected measured values are compared to a respective highest value.

4. The method according to claim 1, wherein the internal combustion engine is switched to an operating mode so that the exhaust gas system is impacted with exhaust gas that has a concentration of pollutants resulting in that the at least one exhaust gas sensor of the first exhaust gas path is exposed to a concentration of pollutants that is higher than a specified limiting value, wherein the concentration of pollutants of the exhaust gas system emitted with the total exhaust gas mass flow remains under the specified limiting value, and wherein the at least one exhaust gas sensor of the second exhaust gas path is calibrated based on a measured value determined with the exhaust gas during an impacting with the exhaust gas of the first exhaust gas path by the at least one exhaust gas sensor, wherein the measured value of the at least one exhaust gas sensor of the second exhaust gas path determined during the impacting of the at least one exhaust gas sensor of the first exhaust gas path is corrected and standardized with the proportionality factor.

5. An exhaust gas system for an internal combustion engine, comprising:
  a control device, a first exhaust gas path and a second exhaust gas path, wherein the first exhaust gas path has at least one exhaust gas post treatment element, the exhaust gas post treatment output of which is reduced relative to an exhaust gas post treatment output of an exhaust gas post treatment element, wherein the first exhaust gas path and the second exhaust gas path are provided with at least one exhaust gas sensor arranged in an exhaust gas flow direction after an exhaust gas post treatment element for the exhaust gas that is generated by the internal combustion engine, wherein the control device is configured to determine pollutant values of a first part of the exhaust gas flow of the exhaust gas mass flow generated by the internal combustion engine measured by at least one exhaust gas sensor of the first exhaust gas path, and to compare them to values of the pollutants of a second part of an exhaust gas mass flow generated by the internal combustion engine determined by an exhaust gas sensor of the second exhaust gas path, and to issue at least one proportionality factor for proportionality between the values of the pollutants determined by the at least one exhaust gas sensor of the first exhaust gas path and the at least one exhaust gas sensor of the second exhaust gas path, and to issue, based on a matching of the values to a predetermined diagnostic value, a diagnosis of the exhaust gas system with the at least one proportionality factor,
  wherein the first exhaust gas path and the second exhaust gas path are configured for the exhaust gas mass flow to be divided and a volumetric flow conducted through the first exhaust gas path is smaller than the volumetric flow conducted through the second exhaust gas path.

6. The exhaust gas system according to claim 5, wherein the first exhaust gas path and the second exhaust gas path are deployed within an exhaust gas post treatment module of the exhaust gas system.

7. The exhaust gas system according to claim 5, wherein the first exhaust gas path and the second exhaust gas path are arranged to being spatially separated from each other.

8. A system, for diagnosing and calibrating an exhaust gas sensor comprising:
  one or more non-transitory computer readable medium; and
  at least one processor communicatively coupled to the one or more non-transitory computer readable medium, the processor operable:
  to read out measured values determined by respective exhaust gas sensors of an exhaust gas system, and to compare the measured values determined by at least one exhaust sensor of a first exhaust gas path to the measured values determined by at least one exhaust gas sensor of a second exhaust gas path, and to calculate at least one proportionality factor based on the comparison, and to issue an error message when the at least one proportionality factor deviates by an amount of a specified limiting value which is greater than a predetermined threshold value,
  wherein an exhaust gas mass flow is divided and a volumetric flow conducted through the first exhaust gas path is smaller than the volumetric flow conducted through the second exhaust gas path.

* * * * *